(12) United States Patent
Hotier et al.

(10) Patent No.: US 6,332,982 B1
(45) Date of Patent: Dec. 25, 2001

(54) APPARATUS FOR REGULATING THE FLOW RATE OF AT LEAST ONE FLUID IN SIMULATED MOVING BED SEPARATION UNITS

(75) Inventors: Gérard Hotier, Chaponost; Albert Le Corre, Houilles; Dominique Humeau, Vienne; Pierre Renard, Saint Nom la Breteche, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/525,454

(22) Filed: Mar. 15, 2000

Related U.S. Application Data

(62) Division of application No. 09/318,574, filed on May 27, 1999, now Pat. No. 6,063,285.

(30) Foreign Application Priority Data

May 29, 1998 (FR) .................................................. 98 06788

(51) Int. Cl.⁷ .................................................. B01D 15/08
(52) U.S. Cl. ........................ 210/198.2; 210/659; 585/805
(58) Field of Search .................................. 210/635, 656, 210/659, 662, 198.2, 672; 208/310 R; 585/805

(56) References Cited

U.S. PATENT DOCUMENTS

| | | | |
|---|---|---|---|
| 5,114,590 | * 5/1992 | Hotier | 210/659 |
| 5,156,736 | 10/1992 | Schoenrock | 210/264 |
| 5,685,992 | * 11/1997 | Cohen | 210/659 |
| 5,755,960 | * 5/1998 | Callebert | 210/659 |
| 5,762,806 | * 6/1998 | Hotier | 210/659 |
| 5,846,411 | * 12/1998 | Hotier | 210/659 |

FOREIGN PATENT DOCUMENTS

| | | | |
|---|---|---|---|
| 0 415 822 | 3/1991 | (EP) | 210/198.2 |
| 2 743 002 | 7/1997 | (FR) | 210/198.2 |

* cited by examiner

*Primary Examiner*—Ernest G. Therkorn
(74) *Attorney, Agent, or Firm*—Millen, White, Zelano & Branigan, P.C.

(57) ABSTRACT

An apparatus and process for regulating the flow rate of at least one fluid or effluent circulating in a simulated moving bed comprises a plurality of beds disposed in a closed loop in at least one chromatographic column (1) and comprising at least one means for recirculating fluid and comprising at least two lines for injecting fluid at a controlled flow rate and at least two lines for withdrawing fluid, one of said withdrawal (extract or raffinate) lines being under flow rate control, the other (60) being under pressure control via at least one control valve (6), and is characterized in that said pressure controlled withdrawal line (60) comprises, in addition to the control valve, comprises at least one restriction means (201) enabling the pressure downstream of at least one of the beds to be reduced. One embodiment of the use of the invention is for separating a xylene isomer.

19 Claims, 6 Drawing Sheets

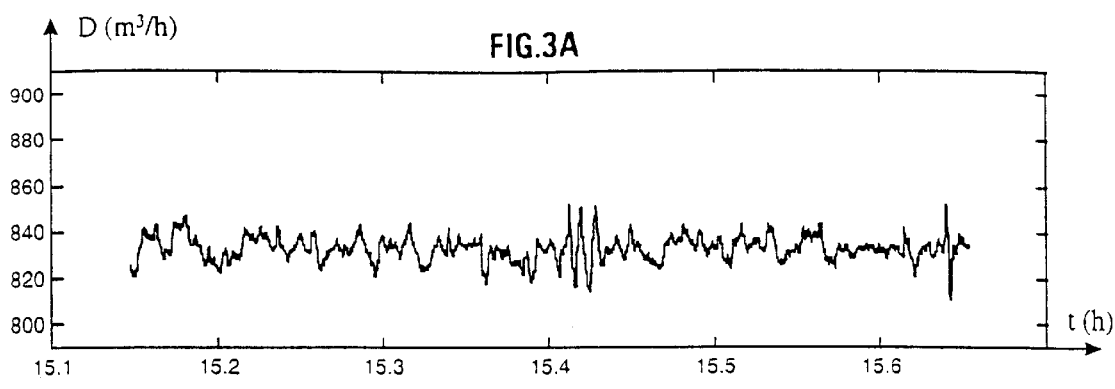
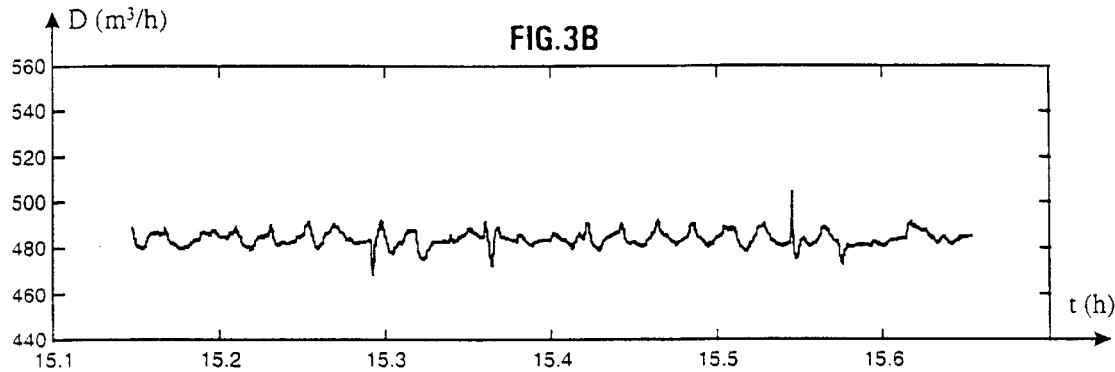
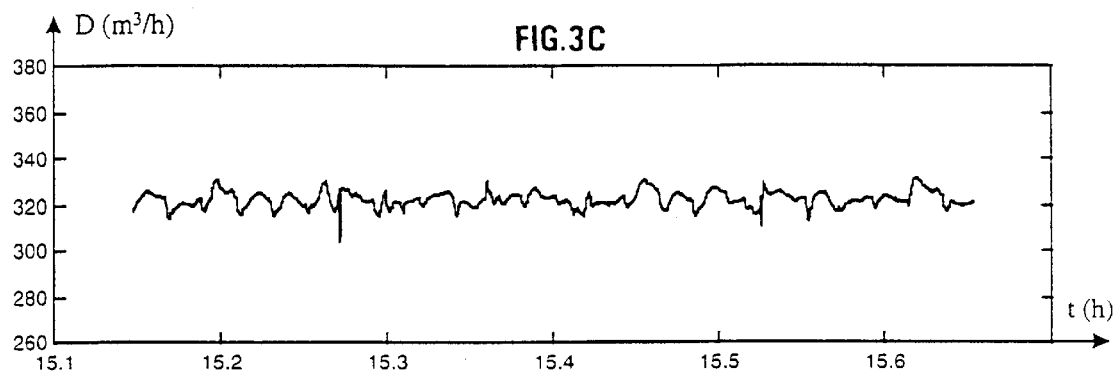
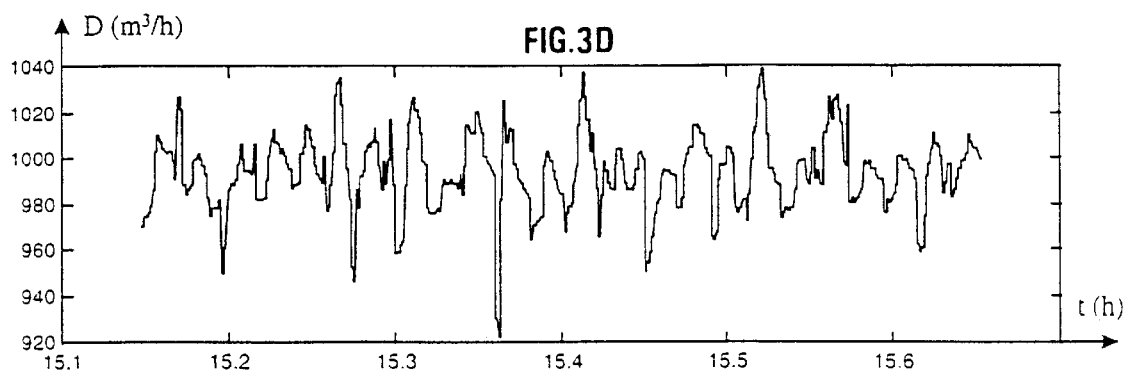

APPARATUS FOR REGULATING THE FLOW RATE OF AT LEAST ONE FLUID IN SIMULATED MOVING BED SEPARATION UNITS

This is a division of application Ser. No. 09/318,574 filed May 27, 1999, now U.S. Pat. No. 6,063,285.

FIELD OF THE INVENTION

The invention relates to an apparatus and to a process for indirect regulation of the flow rate of at least one fluid, for example an effluent, in a chromatographic zone containing a fixed phase, for example an adsorbent or molecular sieve. More particularly, it enables pressures to be produced which are within a predetermined pressure range upstream and downstream of one or preferably a plurality of regulating valves in a counter-current or co-current simulated moving bed adsorption zone.

It is of particular application to separating at least one xylene isomer, in particular para-xylene from a hydrocarbon feed containing it.

BACKGROUND OF THE INVENTION

The prior art is illustrated in European patent EP-A-0 415 822, U.S. Pat. No. 5,156,736 and French patent FR-A-2 743 002 which describes the most effective implementation.

A simulated moving bed comprises at least three chromatographic zones, advantageously four or five, each of the zones being constituted by at least one column or column section. At least one point between two zones acts to inject a feed to be fractionated and at least one point between two zones acts to inject an eluent or desorbent or solvent. Further, the simulated moving bed comprises at least one point for withdrawing an extract between the eluent injection point and the feed injection point located downstream in the desorbent circulation direction and at least one point for withdrawing a raffinate between each mixture injection point and the eluent injection point located downstream in the direction of desorbent circulation.

The set of columns or sections forms at least one closed loop containing at least one recycling pump, between two sections, which pump is flow rate regulated (between the first and last section, for example).

In general, the injection and withdrawal points are periodically shifted by at least one section in the same direction (upstream or downstream).

It is essential to observe the flow rates of the effluents which circulate from one zone to another and which must remain substantially constant in a given zone. A small variation in flow rate, even in a single zone, can have a very large influence on the separation results.

As an example, consider a counter current simulated moving bed comprising four zones with a recycling pump, two incoming streams, the desorbent and the feed, and two outgoing streams, the extract and raffinate.

Zone 1 is located between the desorbent and the extract; zone 2 is located between the extract and the feed; zone 3 is located between the feed and the raffinate; and zone 4 is located between the raffinate and the desorbent. The flow rates in the different zones are as follows when the pump is in zone 1, for example:

Flow rate in zone 1: pump flow rate;
Flow rate in zone 2: flow rate in zone 1−flow rate of extract;
Flow rate in zone 3: flow rate in zone 2+feed flow rate;
Flow rate in zone 4: flow rate in zone 3−raffinate flow rate.

Any errors in the flow rates of the incoming or outgoing streams thus reflect on the recycling flow rate and thus must be controlled with precision.

Each time that one of the incoming or outgoing streams of the loop passes from one to the other side of the recycling pump, for example from a position immediately anterior to a position immediately posterior of the recycling pump when operating in simulated counter-current, two difficulties occur from the point of view of the regularity of the flow rates:

the first difficulty concerns the recycling pump, when it changes zone. It is very important that its flow rate is modified almost instantaneously and that the new flow rate, that of the new zone in which it is to be found, is precisely and stably regulated without the transition from one flow rate to the other being too slow (in the case of damped regulation) or with fluctuations about the new value (in the case of fast response regulation).

This first technical problem is related to changing the zones. It is actually very important that the flow rate passes instantaneously from a first value to a second desired value. As an example, it has been shown that a variation of 0.6% in the recycle flow rate produces a variation of 4.2% in purity. It has been shown that a flow rate regulator which stably regulates the flow rate to which a new set rate is supplied takes a certain time to regulate to the new value. As the transition from one flow rate to another must be very rapid, the gain of the regulator has to be high. In this case, regulation is not very stable. Thus we have to make a choice between rapid but fluctuating regulation or fine and stable regulation but with inertia. Neither of those two solutions is acceptable when regulating a simulated moving bed, which aims to produce high purities.

The second difficulty concerns the flow rate of the stream entering or leaving the unit. The flow rate of that flux must be kept constant, and with very good precision, when its point of injection or withdrawal passes from a low pressure, that of the pump intake, to a high pressure, that of the pump discharge (the pressure difference corresponds to the pressure drop in the group of columns or column sections).

It is very important that these problems are overcome to obtain good separation results.

The solution proposed in the prior art consists of not allowing the regulator to act alone but, by using a computer or any other means which can act on the regulator, to cause that regulator to temporarily stop regulating, simultaneously to cause it to modify its action (pre-positioning the action) such that the new action imposed, such as a percentage valve opening, a current frequency for a motor, a voltage, etc . . . corresponds to the new conditions enabling the flow rate under consideration to be properly regulated and then, but in fact almost immediately, to restart the action of the regulator:

in the case of the recycling pump, to change the flow rate from one zone to another;

in the case of an effluent, to maintain the flow rate in the presence of a large variation in pressure conditions.

Thus good flow rates are obtained without oscillations and almost instantaneously. The ensemble of operations described take between 1/100 and 10 seconds and usually between 1/10 and 5 seconds, depending on the case.

The examples described in the text of the prior art are applicable to a pilot unit comprising 24 beds, for example, and to a single circulating pump.

When the process for regulating the flow rates of the prior art (FR 95/15526) is applied to the unit described in FIGS.

1A, 1B and 2, it can be seen that residual perturbations subsist, in particular in the raffinate flow rate (see FIGS. 3A, 3B, 3D, 3C).

An examination of these figures enables the nature of the problem to be better understood. FIGS. 1A and 1B show how the pressures and flow rates in a closed loop of 24 beds constituting the simulated moving bed are regulated. Two adsorbers 1 and 2 each comprise 12 beds 1.3 m in height and 7.6 m in diameter. Two pumps 9 and 10 circulate liquid inside the adsorbers. A flow meter 3 and a flow rate regulation valve 4 control a flow rate of between 1100 and 3200 m$^3$/h between adsorbers 1 and 2 with a very high precision (0.2%). A pressure controlled raffinate withdrawal valve 6 maintains a set pressure 5 at the intake of pump 9. A control valve 8 maintains a set pressure 7 at the inlet to pump 10. With reference to a cycle of 24 periods where the desorbent is injected into the first bed of adsorber 1, control valve 6 is in direct communication with adsorber 2 during periods 1 to 3 and 16 to 24 (FIG. 1b) and with adsorber 1 during periods 4 to 15. Between periods 3 and 4 raffinate withdrawal passes from the bottom of adsorber 2 to the head of adsorber 1; between periods 15 and 16, raffinate withdrawal passes from the bottom of adsorber 1 to the head of adsorber 2. On-off valves enable a given bed to be placed in communication with the withdrawal circuit, taking about 2.5 seconds to pass from the open position to the closed position (or the reverse). The average pressure drop in each of the two adsorbers is 4.2 bars. When control valve 6 is connected to the bottom of one of the two adsorbers, it is about 67% open; when it is connected to the head of one of the adsorbers, it is about 55% open, with the time taken to pass from 67% open to 55% open being about 2.5 seconds. In the prior art, the best results are obtained by causing control valve 6 to go to 55% open about 2 seconds before manoeuvring the on-off valves and by maintaining this degree of opening for about 6 seconds; at the end of the 6 seconds, the valve is re-set to automatic by the controller. It should also be noted that the best results are obtained with slightly different anticipation and maintenance times during two transitions from the bottom to the head of the adsorbers. Control valves 4 and 8 are manoeuvred using the same principle, however with different anticipation or retardation and maintenance times.

FIG. 2 shows the arrangement of the withdrawals and injections in the loop. The raffinate withdrawal circuit comprises 24 on-off valves numbered 601 to 612 and 651 to 662 (only valves 601 to 603 and 651 to 653 are shown); these 24 valves are connected to a pressure control valve via lines 60, 61 and 62. The extract withdrawal circuit comprises 24 on-off valves numbered 1201 to 1212 and 1251 to 1262 (only valves 1201 and 1253 are shown), these 24 valves are connected to a flow meter 11 and to a flow rate control valve 12 via lines 120, 121 and 122. The feed injection circuit comprises 24 on-off valves numbered 1301 to 1312 and 1351 to 1362 (only valve 1353 is shown); these 24 valves are connected to a pump 15, a flow meter 14 and to a flow rate control valve 13 via lines 130, 131 and 132. The desorbent injection circuit comprises 24 on-off valves numbered 1601 to 1612 and 1651 to 1662 (only valve 1653 is shown); these 24 valves are connected to a pump 18, to a flow meter 17 and to a flow rate control valve 16 via lines 130, 131 and 132.

FIGS. 3A, 3B, 3C and 3D show recordings of the four principal flow rates during a complete cycle. The set values for the flow rates for the desorbent (FIG. 3A), extract (FIG. 3C), and feed (FIG. 3B) are respectively 830 m$^3$/h, 320 m$^3$/h and 480 m$^3$/h. It can be seen that the amplitudes of the variation about the set value are plus or minus 5 m$^3$/h for the extract and feed and plus or minus 5 m$^3$/h for the desorbent. The average resultant raffinate flow rate (FIG. 3D) is 990 m$^3$/h. for this particular stream, the variations in amplitude are +/−50 m$^3$/h instead of the 20 m$^3$/h which should be expected (sum of the amplitudes of the variation in the other flow rates). Under these conditions, a para-xylene production of 74 t/h was produced, with a purity of 99.87% and a yield of 94.5%.

There are two types of perturbations:
1) Each time raffinate withdrawal is permutated from upstream to downstream of the recirculation pumps, despite pre-positioning of the raffinate control valve and anticipation of its operation so as to take into account the manoeuvring time of several seconds and the pressure difference of several bars, it can be seen that the pressure regulated at the bottom of one of the two adsorbers and the raffinate flow rate undergo a perturbation.
2) Each time another of the principal streams is permutated from the head to the bottom of the adsorber, a minimal residual perturbation can be seen in the flow rate of the stream being permutated, and a perturbation is induced in the raffinate flow rate.

The disadvantages of such perturbations in the raffinate flow rate are:
1) Since the distillation column located downstream of the raffinate control valve is supplied at a pulsed flow rate, it has to be overdimensioned compared with a far more regular supply flow rate.
2) A pulsed raffinate flow rate can cause pulsation in the internal flow rates, particularly in zones 3 and 4 of the simulated moving bed. So as to guarantee that the constituents of the raffinate cannot traverse zone 4, the flow rate in zone 4 has to be reduced, i.e., the desorbent flow rate has to be increased with respect to ideal operation. In order not to reduce the flow rate in zone 3 (and thus the feed flow rate and, in the end, the productivity of the unit), a loss of desired constituent in the extract has to be tolerated which is a little higher than that which would be obtained with ideal operation.

It is thus clear that the prior art cannot produce a highly regular raffinate flow rate, and for the other streams, each change in step gives rise to a small perturbation which is clearly observable in the recordings shown in FIGS. 3A, 3B, 3C and 3D.

SUMMARY OF THE INVENTION

The invention aims to reduce those residual perturbations in the flow rate to a minimum using at least one simple mechanical means. More generally the invention aims to produce, in the separation unit in simulated moving bed separation units, inlet and withdrawal flow rates and internal flow rates which are as constant as possible, and indirectly to use less desorbent and increase the yield.

One particular aim of the invention is to ensure a substantially constant pressure just upstream of the valves regulating the withdrawal streams from the simulated moving bed. A second aim of the invention is to ensure a substantially constant pressure just downstream of the valves regulating injection into the simulated moving bed.

BRIEF DESCRIPTION OF THE DRAWINGS

FIGS. 3A, 3B, 3C, and 3D show recordings of the four principal flow rates during a complete cycle.

DESCRIPTION OF THE PREFERRED EMBODIMENTS

Figure 1A:
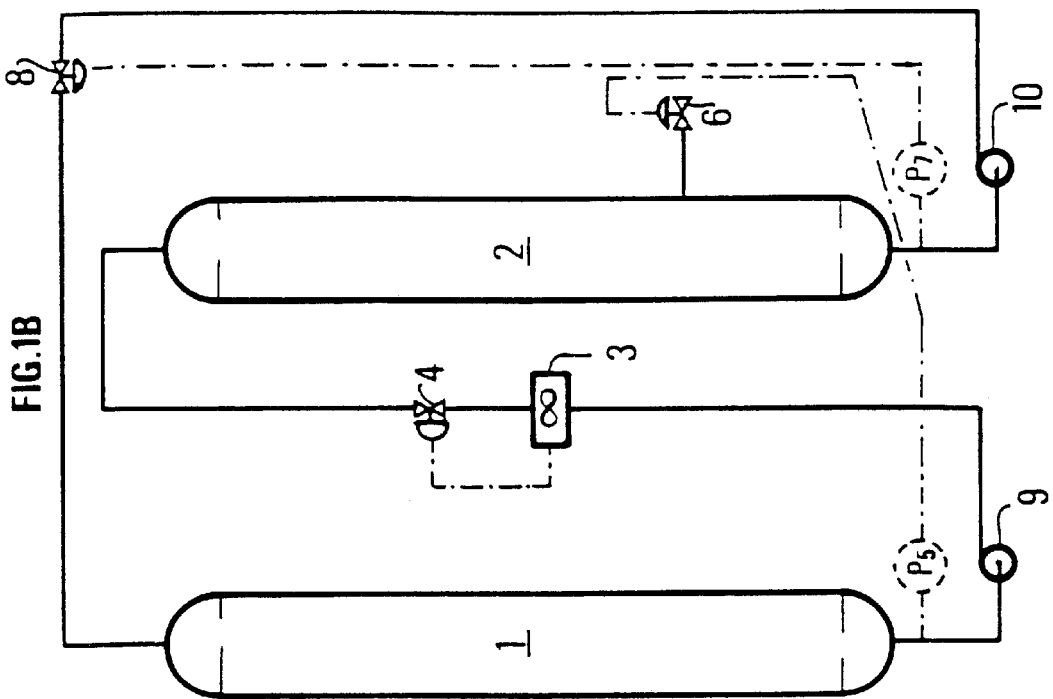
FIGS. 1A, 1B, and 2 show simulated moving bed apparatus.
Figure 1B:
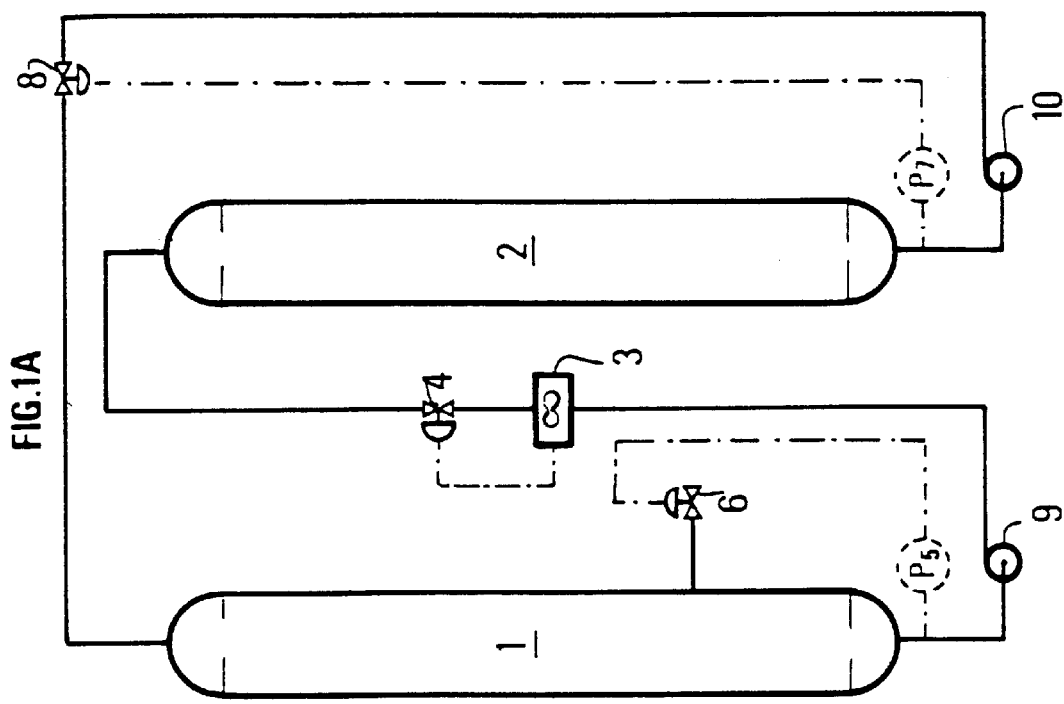

It is known that a sequence for regulating the flow rate or pressure, constituted by a sensor, a regulator generally operating in accordance with the Proportional, Integral, Derivative (PID) algorithm and a valve, must carry out the following functions:

1) Maintain, as closely as possible, the set value when the set value remains fixed (i.e., rapid rejection of perturbations);
2) Return the value to the set value as quickly as possible when said set value is changed (i.e., rapid tracking).

In a simulated moving bed, since a sequence of withdrawals are made from and injections made to a series of beds, in which a fluid is flowing, the pressure upstream of the withdrawal valves or the pressure downstream of the injection valves varies as a function of the injection or withdrawal position. The set value thus remains constant but since the conditions at one of the ports of the regulating valve vary, the PID regulator must thus readjust the position of the valve at each permutation.

The invention thus consists of placing one or more mechanical pressure reducing devices which are advisedly located in the pressure controlled withdrawal circuit (generally the raffinate), and preferably of placing one or more mechanical pressure reducing devices in each of the circuits for withdrawing or introducing into the loop of beds constituting the simulated moving bed.

More precisely, the invention provides an apparatus for regulating the flow rate of a fluid in a simulated moving bed separation unit comprising a plurality of beds disposed in a closed loop in at least one chromatographic column and comprising at least one means for recirculating fluid and comprising at least two lines for injecting fluid at a controlled flow rate and at least two lines for withdrawing fluid, one of said withdrawal (extract or raffinate) lines beinc under flow rate control, the other being under pressure control via at least one control valve, characterized in that said pressure controlled withdrawal line comprises at least one restriction means enabling the pressure downstream of at least one of the beds to be reduced, advantageously between at least one of the beds and the pressure control valve.

In the case of pilot units or small industrial units, a single apparatus per withdrawn or injected stream is required; it is a downstream pressure regulator or a weir in the case of fluid withdrawal; when injecting fluid, an upstream pressure regulator is used. These purely mechanical devices which are well known in the prior art are essentially constituted by a spring and a membrane.

In the case of large industrial units, this type of apparatus is not very suitable: firstly, it is too expensive and secondly, its reaction time is long. It is thus much more practical for the pressure control led withdrawal line to comprise a plurality of restriction means in parallel or in series so as to maintain the pressure upstream of the valve controlling the withdrawn streams within a predetermined range. Preferably, this withdrawal line comprises a plurality of calibrated orifices to ensure a substantially constant pressure downstream of a valve regulating an injection stream or upstream of a valve regulating a withdrawal stream. In a variation, the withdrawal line which comprises a pressure control valve comprises, as the restriction means enabling the pressure to be reduced, at least one valve regulating the pressure differential at the ports of the pressure control valve, said differential pressure regulating valve being located downstream of the pressure control valve and in parallel to the withdrawal line.

In a preferred embodiment, the pressure control withdrawal line comprising at least one restriction means is the raffinate withdrawal line.

The other withdrawal line can comprise a flow rate control valve and at least one restriction means located between at least one of the beds and the (upstream) inlet for the flow rate control withdrawal valve. In a variation, it comprises a flow rate control valve and at least one valve for regulating the differential pressure at the ports of the flow rate control valve, said differential pressure regulation valve being located downstream of the flow rate control valve and in parallel to the withdrawal line.

In a further feature, at least one of the fluid injection lines comprises a flow rate control valve and at least one restriction means located between the (downstream) outlet from the flow rate control valve and at least one bed so as to maintain the pressure downstream of the flow rate control valve within a predetermined pressure range.

In a variation, at least one of the fluid injection lines comprises a flow rate control valve and at least one valve for regulating the pressure differential at the ports of the flow rate control valve, said differential pressure regulation valve being located upstream of the flow rate control valve and in parallel to the injection line. This differential pressure regulation valve thus constitutes the restriction means mentioned above, in which particular case it is located upstream of the flow rate control valve instead of being located downstream.

The invention also provides a process for regulating flow rates using the described apparatus, characterized in that a suitable pressure drop is established by providing at least one restriction means, preferably a plurality of restriction means in parallel or in series, of suitable size, in a line for withdrawing fluid from the column or columns between at least one of the beds and a pressure control valve located in said withdrawal line (extract or raffinate) so as to obtain a pressure upstream of said valve within a range of values in the range from the lowest withdrawal pressure P0 and said value P0 increased by a fraction of the pressure drop in the column, and preferably equal to at most said value P0 increased by 50% of the pressure drop in the column, and particularly preferably equal to at most said value P0 increased by 10% of the pressure drop in the column.

In one feature of the process, a suitable pressure drop is established by providing at least one restriction means, preferably a plurality of restriction means in parallel or in series, of suitable size, in at least one of the lines for injecting fluid into the column or columns between the flow rate control valve located in said injection line (feed or desorbent) and between at least one of said beds so as to obtain a pressure downstream of said valve within a range of values in the range from the highest injection pressure PM and said value PM reduced by a fraction of the pressure drop in the column, preferably at least said value PM reduced by 50% of the pressure drop in the column, and more particularly equal to at least said value PM reduced by 10% of the pressure drop in the column.

In a variation, the pressure drop at the ports of at least one flow rate control valve located in at least one of the injection lines (feed or desorbent) is regulated by placing a differential pressure regulation valve upstream of the flow rate control valve, in parallel to the fluid injection line, so as to obtain a pressure difference at the ports of the flow rate regulation valve in the range from a reference value and said reference value increased by a fraction of the pressure drop in the column, preferably equal to at most said reference value increased by 50% of the pressure drop in the column, and particularly preferably equal to at most said reference value increased by 10% of the pressure drop in the column, said reference value usually being in the range 0.2 to 10 bars, more particularly in the range 0.5 to 2 bars.

In a further feature of the process, a suitable pressure drop is established by providing at least one restriction means, preferably a plurality of restriction means in parallel or in series, of suitable size, in a line for withdrawing fluid of the column or columns between at least one of said beds and a flow rate control valve located in said withdrawal line (extract or raffinate) so as to obtain a pressure upstream of said valve within a range of values in the range from the lowest withdrawal pressure P0 and said value P0 increased by a fraction of the pressure drop in the column, preferably equal to at most said value P0 increased by 50% of the pressure drop in the column, and more particularly preferably equal to at most said value P0 increased by 10% of the pressure drop in the column.

The pressure drop produced by a restriction orifice is proportional to $Krv^2$, where K is a constant, r is the density of the fluid and v is the linear velocity in the orifice. In general, the maximum tolerable velocity in the orifice is of the order of 15 metres per second, and the maximum pressure drop produced by a calibrated orifice does not exceed about 1 bar.

The process can be implemented as follows:

The simplest method would be to use a number of restriction orifices depending on each of the pressure and withdrawal levels for each bed, between each on-off valve and the common withdrawal or extraction line. As an example, if the pressure drop per bed is 0.35 bars and if twelve beds are located in each of the columns, to obtain a constant pressure upstream of a withdrawal control valve, when withdrawing from the first of the beds, five orifices are located in series each providing a pressure drop of 0.7 bars and one orifice providing a pressure drop of 0.35 bars. When withdrawing from the second of the beds, five orifices are located in series each providing a pressure drop of 0.7 bars. When withdrawing from the third of the beds, four orifices are located in series each providing a pressure drop of 0.7 bars and one orifice providing a pressure drop of 0.35 bars. When withdrawing from the fourth of the beds, four orifices are located in series each providing a pressure drop of 0.7 bars. When withdrawing from the fifth of the beds, three orifices are located in series each providing a pressure drop of 0.7 bars and one orifice providing a pressure drop of 0.35 bars. When withdrawing from the sixth of the beds, three orifices are located in series each providing a pressure drop of 0.7 bars. When withdrawing from the seventh of the beds, two orifices are located in series each providing a pressure drop of 0.7 bars and one orifice providing a pressure drop of 0.35 bars. When withdrawing from the eighth of the beds, two orifices are located in series each providing a pressure drop of 0.7 bars. When withdrawing from the ninth of the beds, one orifice is provided to give a pressure drop of 0.7 bars, and one orifice provides a pressure drop of 0.35 bars. When withdrawing from the tenth of the beds, one orifice is provided to give a pressure drop of 0.7 bars. When withdrawing from the eleventh of the beds, one orifice is provided, providing a pressure drop of 0.35 bars. Thus there are 36 calibrated orifices per column and per injected or withdrawn stream. The total number of restriction orifices for the whole loop would thus be 288.

Happily, a more sensible disposition for the above case can reduce the number of restriction orifices per column and per injected or withdrawn stream from 36 to 11: when withdrawing from the first bed, one orifice is provided ensuring a pressure drop of 0.35 bars. When withdrawing from the second bed, no orifice is provided, and in the common line between the second and third bed one orifice is provided ensuring a pressure drop of 0.7 bars. When withdrawing from the third bed, one orifice is provided ensuring a pressure drop of 0.35 bars. When withdrawing from the fourth bed, no orifice is provided, and in the common line between the fourth and fifth bed one orifice is provided ensuring a pressure drop of 0.7 bars. When withdrawing from the fifth bed, one orifice is provided ensuring a pressure drop of 0.35 bars. When withdrawing from the sixth bed, no orifice is provided, and in the common line between the sixth and seventh bed one orifice is provided ensuring a pressure drop of 0.7 bars. When withdrawing from the seventh bed, one orifice is provided ensuring a pressure drop of 0.35 bars.

When withdrawing from the eighth bed, no orifice is provided, and in the common line between the eighth and ninth bed one orifice is provided ensuring a pressure drop of 0.7 bars. When withdrawing from the ninth bed, one orifice is provided ensuring a pressure drop of 0.35 bars. When withdrawing from the tenth bed, no orifice is provided, and in the common line between the tenth and eleventh bed one orifice is provided ensuring a pressure drop of 0.7 bars. When withdrawing from the eleventh bed, one orifice is provided, ensuring a pressure drop of 0.35 bars.

Depending on the tolerated pressure variation range, the number of beds, the number of recirculation pumps in the loop and the manoeuvring time for the control valve, 2 to 30 calibrated orifices can be provided per withdrawal circuit.

The invention will be better understood from the following examples:

EXAMPLE 1

Figure 4:
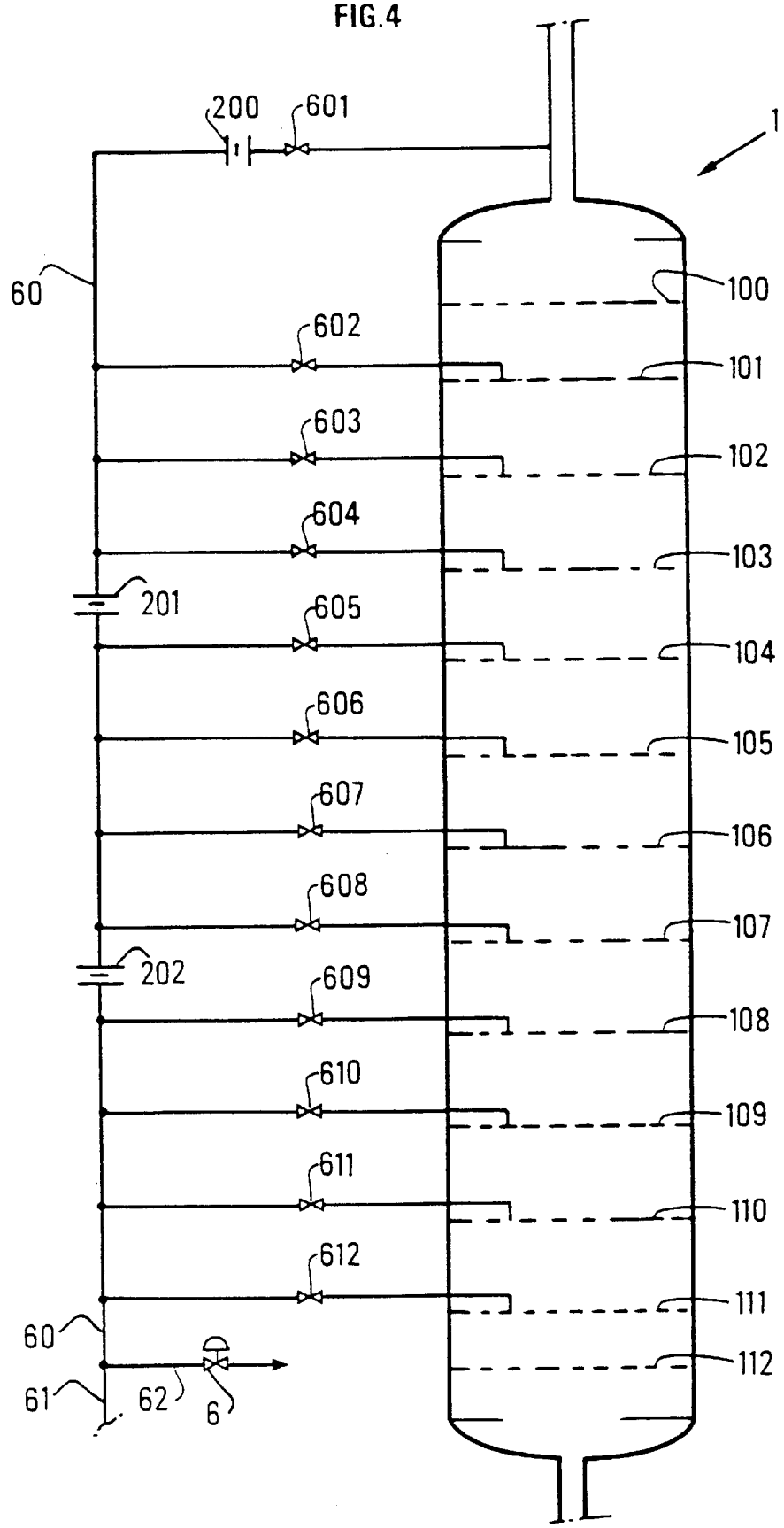
FIGS. 4, 5, and 6 show three embodiments of the present invention.

FIG. 4 shows an embodiment of the invention in the case where about 1bar of pressure variation is tolerated upstream of the raffinate control valve: 6 calibrated orifices are required to obtain a pressure in the range 8.35 to 9.4 bars. Only adsorber 1 is shown in FIG. 4.

Figure 2:
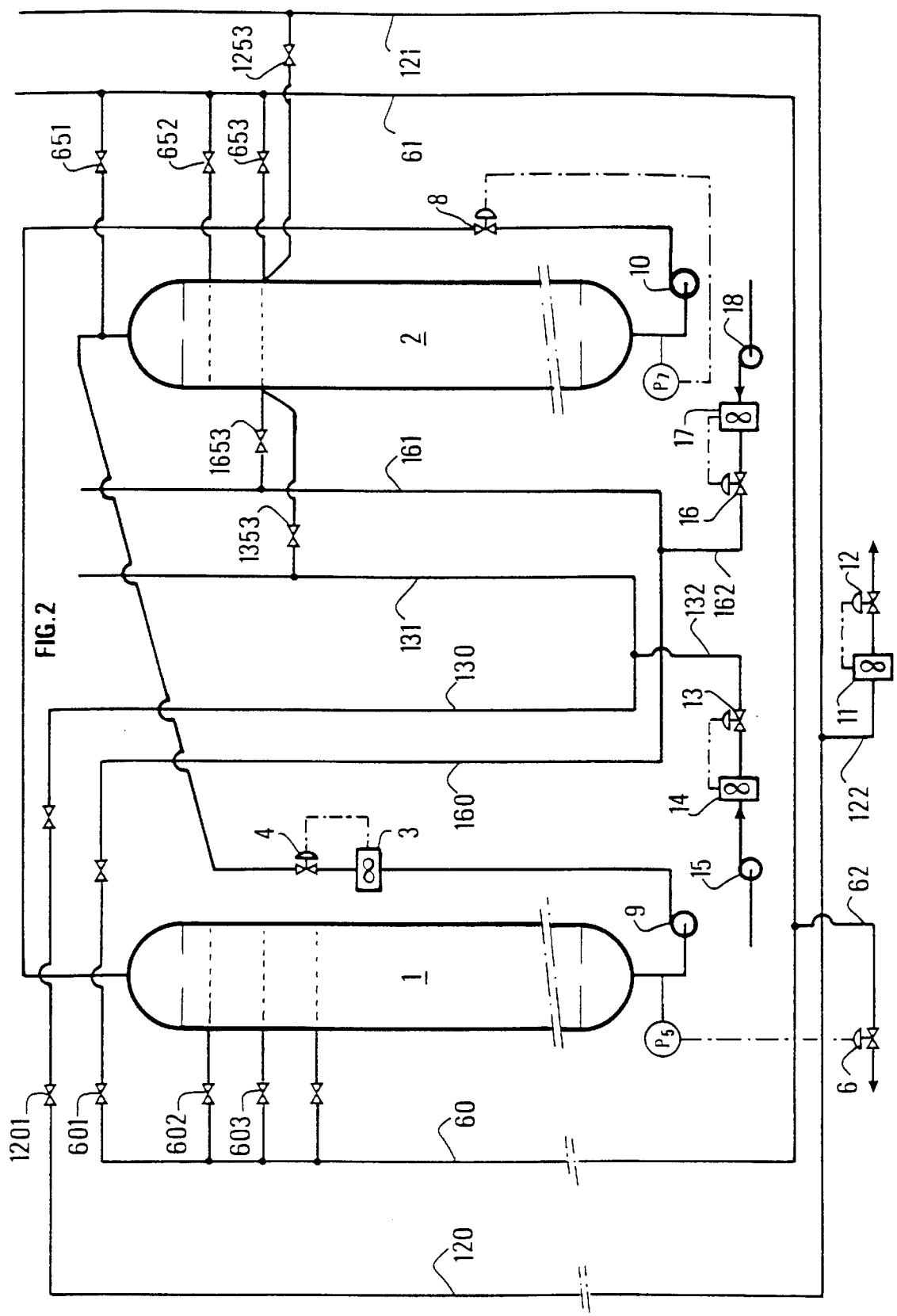

The pressure drop for an average internal flow rate of about 2000 m³/h is 4.2 bars; the average pressure drop across each bed is about 0.35 bars; this pressure drop being distributed in an amount of about 0.27 bars for the molecular sieve and 0.08 bars to traverse one of plates 101 to 111. Plates 101 to 111 also contain a series of holes for distributing the injected or withdrawn principal stream. The diameter of these holes and that of the lines placing the holes in communication with each of four flanges for connection to the exterior of the adsorber have been calculated so that the pressure drop between the interior and exterior of the adsorber is 1 bar. Withdrawal valve 601 is unique since it is directly in communication with the discharge of the recirculation pump 10. In accordance with the invention, three calibrated orifices 200, 201 and 202 have been placed in line 60 (the corresponding orifices placed in line 61 connecting adsorber 2 (FIG. 2) to control valve 6 are not shown in the Figure). Calibrated orifice 200 produces a pressure drop of 1 bar, while calibrated orifices 201 and 202 each produce a pressure drop of 1.4 bars. To simplify the description, a series of two calibrated orifices each producing a pressure drop of 0.7 bars has been termed "calibrated orifice 201 and calibrated orifice 202". The pressure balance following the raffinate withdrawal position is given below:

Period 4: raffinate is withdrawn via valve 601; pressure in recirculation line 13.2 bars; pressure downstream of orifice 200 12.2 bars; pressure downstream of orifice 201 10.8 bars; pressure downstream of orifice 202 9.4 bars.

Period 5: raffinate is withdrawn via valve 602: pressure in adsorber at plate 101 12.85 bars, pressure upstream of orifice 201 11.85 bars; pressure downstream of orifice 201 10.45 bars; pressure downstream of orifice 202 9.05 bars.

Period 6: raffinate is withdrawn via valve 603: pressure in adsorber at plate 102 12.5 bars; pressure upstream of orifice 201 11.5 bars; pressure downstream of orifice 201 10.1 bars; pressure downstream of orifice 202 8.65 bars.

Period 7: raffinate is withdrawn via valve 604: pressure in adsorber at plate 103 12.15 bars; pressure upstream of orifice 201 11.15 bars; pressure downstream of orifice 201 9.75 bars; pressure downstream of orifice 202 8.35 bars.

Period 8: raffinate is withdrawn via valve 605: pressure in adsorber at plate 104 11.8 bars; pressure upstream of orifice 202 10.8 bars; pressure downstream of orifice 202 9.4 bars.

Period 9: raffinate is withdrawn via valve 606: pressure in adsorber at plate 105 11.45 bars; pressure upstream of orifice 202 10.45 bars; pressure downstream of orifice 202 9.05 bars.

Period 10: raffinate is withdrawn via valve 607: pressure in adsorber at plate 106 11.1 bars; pressure upstream of orifice 202 10.1 bars; pressure downstream of orifice 202 8.7 bars.

Period 11: raffinate is withdrawn via valve 608: pressure in adsorber at plate 107 10.75 bars; pressure upstream of orifice 202 9.75 bars; pressure downstream of orifice 202 8.35 bars.

Period 12: raffinate is withdrawn via valve 609: pressure in adsorber at plate 108 10.4 bars; pressure downstream of orifice 202 9.4 bars.

Period 13: raffinate is withdrawn via valve 610: pressure in adsorber at plate 109 10.05 bars; pressure downstream of orifice 202 9.05 bars.

Period 14: raffinate is withdrawn via valve 611: pressure in adsorber at plate 110 9.7 bars; pressure downstream of orifice 202 8.7 bars.

Period 15: raffinate is withdrawn via valve 612: pressure in adsorber at plate 111 9.35 bars; pressure downstream of orifice 202 8.35 bars. The pressure measured between orifice 202 and control valve 6 varies between 8.35 and 9.4 bars. Control valve opening 64.5% to 67%. The pre-positioning and maintaining the valve for 5 seconds between steps 3 and 4, 7 and 8, 11 and 12, 15 and 16, 19 and 20, 23 and 24. The observed fluctuation in raffinate flow rate was about +/−30 m³/h about the average value, With this modification, the flow rates of the desorbent and raffinate were reduced by 20 m³/h while retaining identical performances; it could also be seen that the loss of desorbent at the head of the raffinate distillation column was also reduced by about 30% because of more stable operation.

EXAMPLE 2

Figure 5:
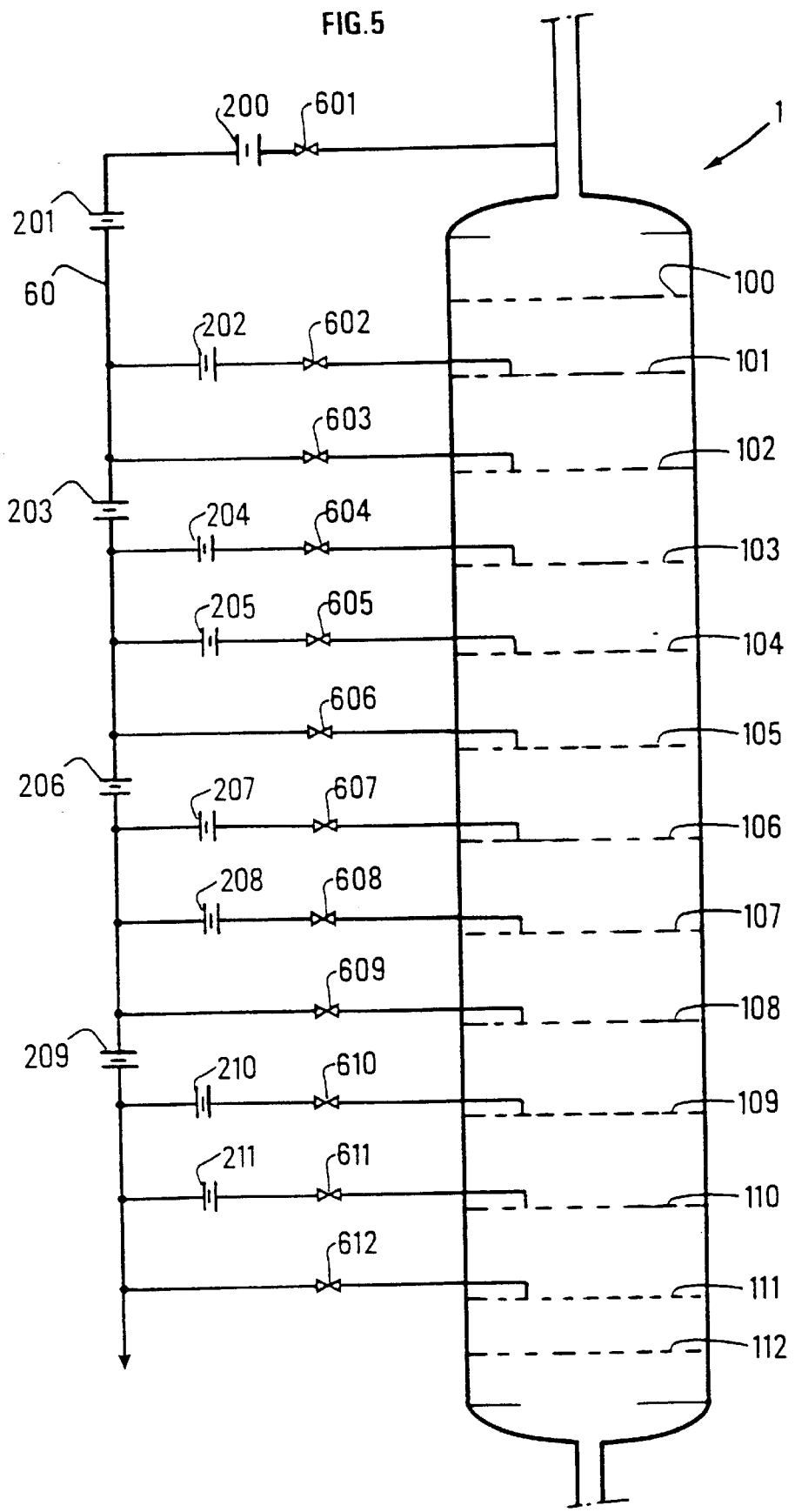

FIG. 5 shows an example of an implementation of the invention when a pressure variation of about 0.1 bars is tolerated just upstream of raffinate control valve 6: thus 24 calibrated orifices are required to obtain a pressure of the order of 8.35 bars upstream of said valve. In accordance with the invention, twelve calibrated orifices 200 to 211 are placed in line 60 (the corresponding symmetrical orifices placed in line 61 connecting adsorber 2 to control valve 6 are not shown in the Figure). Calibrated orifices 203, 206 and 209 each produce a pressure drop of 1.05 bars; calibrated orifice 201 produces a pressure drop of 1 bar; calibrated orifices 200, 204, 207 and 211 each produce a pressure drop of 0.7 bars; calibrated orifices 202, 205, 208 and 212 each produce a pressure drop of 0.35 bars. The pressure balance following the raffinate withdrawal position is as follows:

Period 4: raffinate is withdrawn via valve 601: pressure in recirculation line 13.2 bar; pressure downstream of orifices 200 and 201 11.5 bars; pressure downstream of orifice 203 10.45 bars; pressure downstream of orifice 206 9.4 bars; pressure downstream of orifice 209 8.35 bars.

Period 5: raffinate is withdrawn via valve 602: pressure in adsorber at plate 101 12.85 bar; pressure upstream of orifice 202 11.85 bars; pressure downstream of orifice 202 11.5 bars; pressure downstream of orifice 203 10.45 bars; pressure downstream of orifice 206 9.4 bars; pressure downstream of orifice 209 8.35 bars.

Period 6: raffinate is withdrawn via valve 603: pressure in adsorber at plate 102 12.5 bar; pressure upstream of orifice 203 11.5 bars; pressure downstream of orifice 203 10.45 bars; pressure downstream of orifice 206 9.4 bars; downstream of orifice 209 8.35 bars.

Period 7: raffinate is withdrawn via valve 604: pressure in adsorber at plate 103 12.15 bar; pressure upstream of orifice 204 11.15 bars; pressure downstream of orifice 204 10.45 bars; pressure downstream of orifice 206 9.4 bars; pressure downstream of orifice 209 8.35 bars.

Period 8: raffinate is withdrawn via valve 605: pressure in adsorber at plate 104 11.8 bar; pressure upstream of orifice 205 10.8 bars; pressure downstream of orifice 205 10.45 bars; pressure downstream of orifice 206 9.4 bars; pressure downstream of orifice 209 8.35 bars.

Period 9: raffinate is withdrawn via valve 606: pressure in adsorber at plate 105 11.45 bar; pressure upstream of orifice 206 10.45 bars; pressure downstream of orifice 206 9.4 bars; pressure downstream of orifice 209 8.35 bars.

Period 10: raffinate is withdrawn via valve 607: pressure in adsorber at plate 106 11.1 bar; pressure upstream of orifice 207 10.1 bars; pressure downstream of orifice 207 9.4 bars; pressure downstream of orifice 209 8.35 bars.

Period 11: raffinate is withdrawn via valve 608: pressure in adsorber at plate 107 10.75 bar; pressure upstream of orifice 208 9.75 bars; pressure downstream of orifice 208 9.4 bars; pressure downstream of orifice 209 8.35 bars.

Period 12: raffinate is withdrawn via valve 609: pressure in adsorber at plate 107 10.4 bar; pressure upstream of orifice 209 9.4 bars; pressure downstream of orifice 209 8.35 bars.

Period 13: raffinate is withdrawn via valve 610: pressure in adsorber at plate 108 10.05 bar; pressure upstream of orifice 211 9.05 bars; pressure downstream of orifice 211 8.35 bars.

Period 14: raffinate is withdrawn via valve 611: pressure in adsorber at plate 109 9.7 bar; pressure upstream of orifice 212 8.7 bars; pressure downstream of orifice 212 8.35 bars.

Period 15: raffinate is withdrawn via valve 612: pressure in adsorber at plate 110 9.35 bar; pressure upstream of regulation valve 6 8.35 bars.

The pressure measured just upstream of control valve 6 is 8.35 bars with fluctuations of less than 0.1 bars. The control valve was about 67% open. Pre-positioning of control valve 6 was no longer necessary. The observed fluctuation of the raffinate flow rate was about +/−25 m³/h about the average value. The improvement over Example 1 was not very substantial: the residual perturbations essentially originated from the sum of the fluctuations in the other streams.

EXAMPLE 3

All of the injection and all of the withdrawal points are equipped in accordance with the invention: in the withdrawal circuit, a pressure variation of the order of 1 bar is tolerated; thus 6 calibrated orifices are placed in the circuit; in the raffinate circuit, a variation of only 0.35 bars is tolerated and thus 12 calibrated orifices are placed in this circuit.

Figure 6:
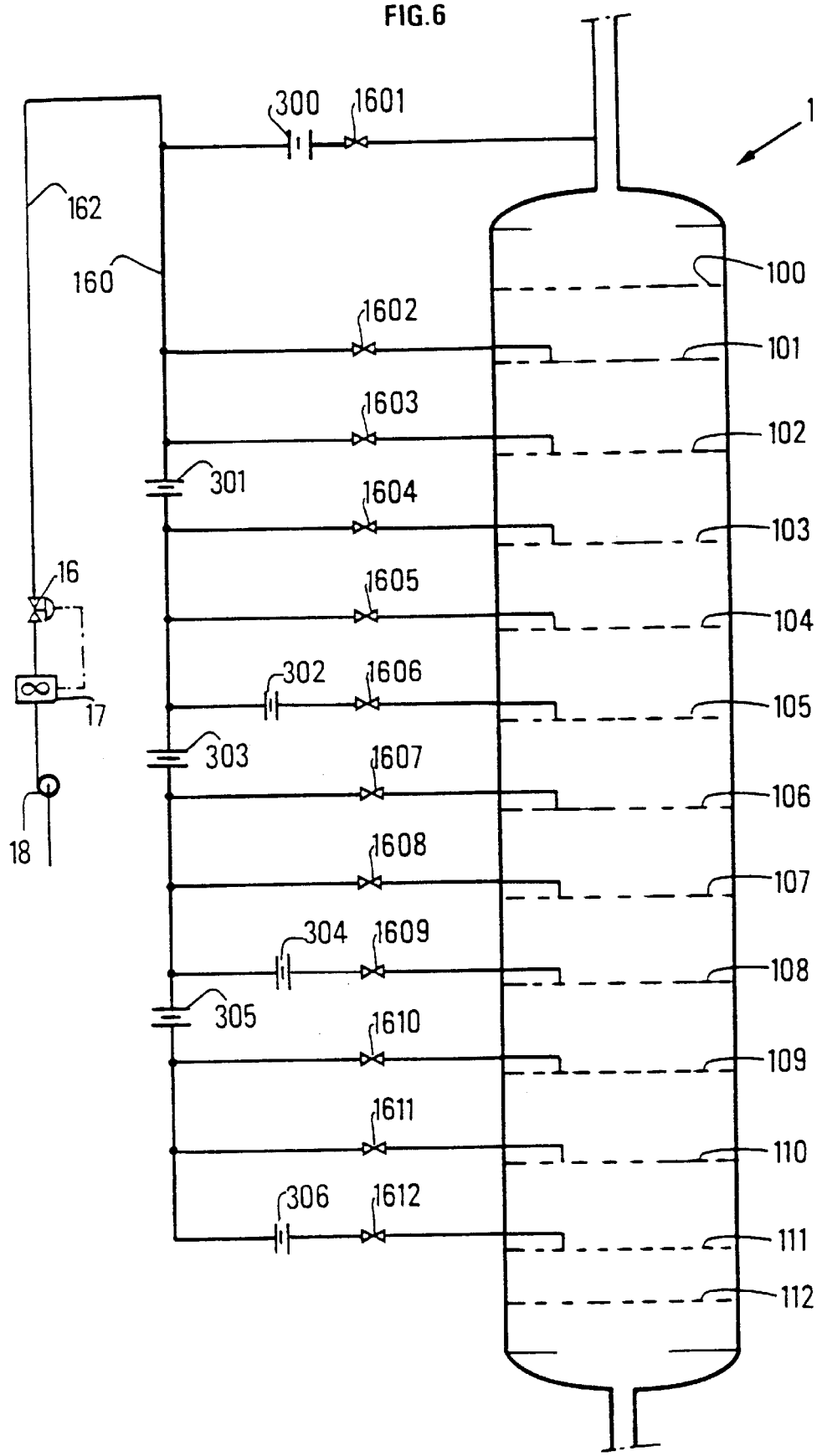

In the feed circuit, a pressure variation of the order of 1 bar is tolerated, thus 4 calibrated orifices are placed in this circuit: in fact, the equivalent to orifice 200 in FIG. 4 is not necessary in this case. FIG. 6 shows an example of an embodiment of the invention where a pressure variation of only 0.35 bars downstream of desorbent control valve 16 is tolerated. Only adsorber 1 is shown with its 7 orifices numbered 300 to 306, also the desorbent injection circuit comprising 14 orifices. Calibrated orifices 300, 302, 304, 306 each produce a pressure drop of 0.35 bars; calibrated orifice 301 produces a pressure drop of 0.7 bars; calibrated orifices 303 and 305 each produce a pressure drop of 1.05 bars. To simplify the description, a series of two calibrated orifices each producing a pressure drop of 0.525 bars is termed a "calibrated orifice 303". It should also be noted that line 162 is connected to the top part of line 160 and not to the bottom part as in FIG. 2. The pressure balance following the raffinate withdrawal position is as follows:

Period 1: desorbent is injected via valve 1601: pressure in the recirculation line 13.2 bars; pressure upstream of orifice 300 13.5 bars.

Period 2: desorbent is injected via valve 1602: pressure in adsorber at plate 101 12.85 bars; pressure at valve 1602 13.5 bars.

Period 3: desorbent is injected via valve 1603: pressure in adsorber at plate 102 12.5 bars; pressure at valve 1603 13.5 bars.

Period 4: desorbent is injected via valve 1604: pressure in adsorber at plate 103 12.15 bars; pressure at valve 1604 13.15 bars; pressure upstream of orifice 301 13.85 bars.

Period 5: desorbent is injected via valve 1605: pressure in adsorber at plate 104 11.8 bars; pressure at valve 1605 12.8 bars; pressure upstream of orifice 301 13.5 bars.

Period 6: desorbent is injected via valve 1606: pressure in adsorber at plate 105 11.45 bars; pressure at valve 1606 12.45 bars; pressure upstream of orifice 302 12.8 bars; pressure upstream of orifice 301 13.5 bars.

Period 7: desorbent is injected via valve 1607: pressure in adsorber at plate 106 11.1 bars; pressure at valve 1607 12.1 bars; pressure upstream of orifice 303 13.15 bars; pressure upstream of orifice 301 13.85 bars.

Period 8: desorbent is injected via valve 1608: pressure in adsorber at plate 107 10.75 bars; pressure at valve 1608 11.75 bars; pressure upstream of orifice 303 12.8 bars; pressure upstream of orifice 301 13.5 bars.

Period 9: desorbent is injected via valve 1609: pressure in adsorber at plate 108 10.4 bars; pressure at valve 1609 11.4 bars; pressure upstream of orifice 304 11.75 bars; pressure upstream of orifice 303 12.8 bars; pressure upstream of orifice 301 13.5 bars.

Period 10: desorbent is injected via valve 1610: pressure in adsorber at plate 109 10.05 bars; pressure at valve 1610 11.05 bars; pressure upstream of orifice 305 12.1 bars; pressure upstream of orifice 303 13.15 bars; pressure upstream of orifice 301 13.85 bars.

Period 11: desorbent is injected via valve 1611: pressure in adsorber at plate 110 9.7 bars; pressure at valve 1611 10.7 bars; pressure upstream of orifice 305 11.75 bars; pressure upstream of orifice 303 12.8 bars; pressure upstream of orifice 301 13.5 bars.

Period 12: desorbent is injected via valve 1612: pressure in adsorber at plate 111 9.35 bars; pressure at valve 1612 10.35 bars; pressure upstream of orifice 306 10.7 bars; pressure upstream of orifice 305 11.75 bars; pressure upstream of orifice 303 12.8 bars; pressure upstream of orifice 301 13.5 bars.

The pressure measured just downstream of control valve 16 is in the range 13.5 to 13.85 bars. The control valve is between 46% and 47% open. Pre-positioning of control valve 16 is no longer necessary. Pre-positioning of control valves 4, 8, 12 and 13 remains necessary.

The observed fluctuation of the raffinate flow rate was about 20+/−10 m$^3$/h about the average value. The observed fluctuation in the desorbent flow rate was less than +/−5 m$^3$/h about the average value. The fluctuations in the feed and extract flow rates observed about the average value was about +/−2 m$^3$/h.

The improvement over the prior art was very substantial: by reducing the desorbent and raffinate flow rates by 40 m$^3$/h, while keeping the internal flow rates in zones 1, 2 and 3 constant, the purity remained identical and an increase in yield of 0.45% was observed, which meant that production increased by 0.3 t/h.

The invention includes a further advantage: during permutation from one bed to the next, and for a brief period (about 2 seconds), there is the possibility of a by-pass between these two beds (the next valve may open before the previous valve closes). To prevent this undesirable by-pass, an anti-return valve can be installed between each on-off valve and the common injection and withdrawal lines. This causes the following problems: these valves are mechanically very highly strained (a large number of cycles between two stoppages) and can be damaged by jolts which they may receive; in particular, those valves located in the bed where the pressure is the lowest for the withdrawals and those located on the bed where the pressure is the highest for injections suffer very violent shocks compared with all of the others. Restriction orifices, while not completely eliminating the possibility of by-pass, at least limit it considerably.

When the unit is pushed to a maximum (typically 110% to 120%) of its nominal capacity or when, in contrast, it has to function at a minimum of its capacity (typically 55% to 60% of its nominal capacity), the ratio of the flow rates in these two cases varies from one to two. To a first approximation, the pressure drop in the beds is proportional to the flow rates. The result is that restriction orifices adapted to their nominal capacity no longer completely fulfill their role. When long term operation at a capacity which is significantly different to the nominal capacity is envisaged, it is important to replace them with another set of orifices adapted to the new operating flow rates.

The application of the invention has been described above for units comprising a plurality of on-off valves carrying out the injections or withdrawals. The invention can also be applied to "Sorbex" type units. In these units, a "rotary" valve places each of the beds of the simulated moving bed in communication with 4 to 7 injection and withdrawal streams. One of the particular features of Sorbex type units is that they only have one connection line per bed. In the case of a 24 bed unit disposed in two adsorbers each with 12 beds, for example, at least 16 orifices would be needed, located in the 16 outlets with the highest pressure to produce a pressure variation of the order of 1 bar upstream of the raffinate and extract control valves. For the injection circuits, the pressure difference downstream of the feed and desorbent control valves would thus be substantially increased, since injecting into the beds at the adsorber head would mean injecting into the highest pressures in the loop, which would further increase the pressure drops in the restriction orifices; this would, of course, result in disadvantages which would be clear to the skilled person.

Two alternatives thus present themselves: thanks to a modification of this type of unit. the preferred apparatus of the invention can be used; a further possibility consists of using a variation of the invention.

To use the preferred apparatus of the invention, two rotary valves must be used: one dedicated to injections, the other to withdrawals. Further, two lines per bed are necessary: one connecting the bed to the injection rotary valve, and the other to the withdrawal rotary valve. In this way, the restriction orifices adapted to withdrawal can be placed in the lines connecting each of the beds to the rotary valve dedicated to withdrawals and, independently, the restriction orifices adapted to injections can be placed in the lines connecting each of the beds to the rotary valve dedicated to injection.

In a variation of the invention, the restriction means can be a valve for regulating the differential pressure at the ports of at least one and preferably to the ports of each of the flow rate or pressure control valves. Naturally, whatever the simulated moving bed unit type, solutions consisting of blending the preferred apparatus of the invention and the variation are always possible.

It should be noted that at a constant flow rate and opening of a regulation valve (for example when it is in manual mode), if a pressure perturbation is produced downstream of the valve it is reflected upstream (and conversely). For a liquid injection valve which has to operate at a constant flow rate and with as constant as possible a percentage opening, regulation of the differential pressure at the ports of the flow rate control valve can avoid placing a series of restriction orifices in the injection lines, for example (in the case of Sorbex type units on each of the lines connecting each bed to the rotary valve). In this case, the different pressure levels will be retransmitted upstream of the injection flow rate control valves.

At the ports of the desorbent flow rate regulation sequence constituted by the flow meter and the control valve, a differential pressure sensor is installed. This drives a second control valve which enables liquid to be returned upstream of the desorbent pump. When the rotary valve advances from one position, the drop or increase in pressure between two consecutive beds will be reflected upstream of the flow rate control valve. Opening or closing the differential pressure control valve will thus maintain the pressure drop constant across the flow rate control valve. In the particular case where desorbent injection passes from upstream to downstream of the recycling pumps, pre-positioning of the valve described in the prior art will, of course, be employed. Adding the differential pressure control valve does not simply displace the problem from one valve to another strictly identical valve: since the liquid pressure is regulated in parallel from the injection line, a low liquid withdrawal between the pump and flow rate control valve will be sufficient to reduce the pressure upstream of the flow rate control valve.

Withdrawals can be treated similarly: differential pressure control at the ports of the control valve will be effected by placing a second control valve downstream of said control valve. In parallel.

However, in the preferred apparatus of the invention (a series of orifices), which reacts instantaneously, a differential pressure regulation sequence always has a reaction time, and small residual oscillations in the flow rate persist, further the actions of two coupled control valves are more difficult to regulate than those of a single valve.

What is claimed is:

1. An apparatus for regulating the flow rate of a fluid in a simulated moving bed separation unit comprising a plurality of beds disposed in a closed loop in at least one chromatographic column (1) and comprising at least one means for recirculating fluid (9) and comprising at least two lines for injecting fluid at a controlled flow rate and at least two lines for withdrawing fluid, one of said withdrawal (extract or raffinate) lines being under flow rate control, the other (60) being under pressure control via at least one control valve (6), characterized in that said pressure controlled withdrawal line (60) comprises at least one restriction means (201) enabling the pressure downstream of at least one of the beds to be reduced.

2. An apparatus according to claim 1, in which the pressure controlled withdrawal line comprises at least one restriction means enabling the pressure between at least one of the beds and the pressure control valve to be reduced.

3. A flow rate regulation apparatus according to claim 2, in which at least one of the injection lines (130) comprises a flow rate control valve (13) and at least one restriction means located between the (downstream) outlet from the flow rate control valve and at least one bed so as to maintain the pressure downstream of the flow rate control valve within a predetermined range.

4. A flow rate regulation apparatus according to claim 2, in which at least one of the injection lines comprises a flow rate control valve and at least one valve for regulating the pressure differential at the ports of the flow rate control valve, said differential pressure regulation valve being located upstream of the flow rate control valve and in parallel to the injection line.

5. A flow rate regulation apparatus according to claim 2, in which the flow rate withdrawal line (120) comprises a flow rate control valve (12) and at least one restriction means located between at least one of the beds and the (upstream) inlet to the flow rate controlled withdrawal valve.

6. A flow rate regulation apparatus according to claim 2, in which the flow rate withdrawal line comprises a flow rate control valve and at least one valve for regulating the pressure differential at the ports of the flow rate control valve, said differential pressure regulation valve being located downstream of the flow rate control valve and in parallel to the injection line.

7. An apparatus according to claim 1, in which the pressure controlled withdrawal line comprises a plurality of restriction means in parallel or in series so as to maintain the pressure upstream of the control valve for withdrawn streams within a predetermined range.

8. A flow rate regulation apparatus according to claim 7, in which at least one of the injection lines (130) comprises a flow rate control valve (13) and at least one restriction means located between the (downstream) outlet from the flow rate control valve and at least one bed so as to maintain the pressure downstream of the flow rate control valve within a predetermined range.

9. A flow rate regulation apparatus according to claim 7, in which at least one of the injection lines comprises a flow rate control valve and at least one valve for regulating the pressure differential at the ports of the flow rate control valve, said differential pressure regulation valve being located upstream of the flow rate control valve and in parallel to the injection line.

10. A flow rate regulation apparatus according to claim 7, in which the flow rate withdrawal line (120) comprises a flow rate control valve (12) and at least one restriction means located between at least one of the beds and the (upstream) inlet to the flow rate controlled withdrawal valve.

11. A flow rate regulation apparatus according to claim 7, in which the flow rate withdrawal line comprises a flow rate control valve and at least one valve for regulating the pressure differential at the ports of the flow rate control valve, said differential pressure regulation valve being located downstream of the flow rate control valve and in parallel to the injection line.

12. A flow rate regulation apparatus according to claim 1, in which the pressure controlled withdrawal line contains the raffinate.

13. A flow rate regulation apparatus according to claim 1, in which at least one of the injection lines (130) comprises a flow rate control valve (13) and at least one restriction means located between the (downstream) outlet from the flow rate control valve and at least one bed so as to maintain the pressure downstream of the flow rate control valve within a predetermined range.

14. A flow rate regulation apparatus according to claim 1, in which at least one of the injection lines comprises a flow rate control valve and at least one valve for regulating the pressure differential at the ports of the flow rate control valve, said differential pressure regulation valve being located upstream of the flow rate control valve and in parallel to the injection line.

15. A flow rate regulation apparatus according to claim 1, in which the flow rate withdrawal line (120) comprises a flow rate control valve (12) and at least one restriction means located between at least one of the beds and the (upstream) inlet to the flow rate controlled withdrawal valve.

16. A flow rate regulation apparatus according to claim 15, in which said withdrawal line which comprises a pressure control valve comprises, as the restriction means enabling the pressure to be reduced, at least one valve for regulating the pressure differential at the ports of the pressure control valve, said differential pressure regulation valve being located downstream of the pressure control valve and in parallel to the withdrawal line.

17. A flow rate regulation apparatus according to claim 1, in which the other withdrawal line comprises a flow rate control valve and at least one valve for regulating the pressure differential at the ports of the flow rate control valve, said differential pressure regulation valve being located downstream of the flow rate control valve and in parallel to the injection line.

18. A flow rate regulation apparatus according to claim 17, in which said withdrawal line which comprises a pressure control valve comprises, as the restriction means enabling the pressure to be reduced, at least one valve for regulating the pressure differential at the ports of the pressure control valve, said differential pressure regulation valve being located downstream of the pressure control valve and in parallel to the withdrawal line.

19. A flow rate regulation apparatus according to claim 1, in which said withdrawal line which comprises a pressure control valve comprises, as the restriction means enabling the pressure to be reduced, at least one valve for regulating the pressure differential at the ports of the pressure control valve, said differential pressure regulation valve being located downstream of the pressure control valve and in parallel to the withdrawal line.

* * * * *